United States Patent [19]

Terashima et al.

[11] Patent Number: 4,839,278

[45] Date of Patent: Jun. 13, 1989

[54] INTEGRAL MULTILAYER ANALYTICAL ELEMENT FOR MEASUREMENT OF ALKALINE PHOSPHATASE ACTIVITY

[75] Inventors: Kaoru Terashima; Takushi Miyazako; Harumi Katsuyama, all of Asaka, Japan

[73] Assignee: Fuji Photo Film Co., Ltd., Kanagawa, Japan

[21] Appl. No.: 866,349

[22] Filed: May 22, 1986

[30] Foreign Application Priority Data

May 23, 1985 [JP] Japan ................................ 60-111187

[51] Int. Cl.$^4$ ........................ C12Q 1/42; G01N 31/22
[52] U.S. Cl. ........................................ 435/21; 422/56; 422/57; 422/58; 435/805
[58] Field of Search ............... 422/56, 57, 58; 435/21, 435/805

[56] References Cited

U.S. PATENT DOCUMENTS 3,992,158 11/1976 Przybylowicz et al. ......... 422/58 X
4,555,484 11/1985 LaRossa et al. ...................... 435/21

FOREIGN PATENT DOCUMENTS 116361 8/1984 European Pat. Off. .

Primary Examiner—Barry S. Richman
Assistant Examiner—Jill Johnston
Attorney, Agent, or Firm—Jules E. Goldberg

[57] ABSTRACT

An integral multilayer analytical element for the measurement of alkaline phosphatase activity, which comprises a porous spreading layer containing a self-developable substrate in response to contact with alkaline phosphatase, a buffer layer containing a diffusion-resistant base and a support in a laminated form.

12 Claims, No Drawings

INTEGRAL MULTILAYER ANALYTICAL ELEMENT FOR MEASUREMENT OF ALKALINE PHOSPHATASE ACTIVITY

BACKGROUND OF THE INVENTION

1. Field of the Invention

The present invention relates to an integral multilayer analytical element for use in the measurement of alkaline phosphatase activity in a liquid sample, and more particularly to an integral multilayer analytical element for use in the measurement of alkaline phosphatase activity in aqueous liquid samples, particularly in body fluids in the course of clinical tests.

2. Description of Prior Arts

It is very important to measure alkaline phosphatase activity in human body fluids in clinical tests. The measurement of the activity of alkaline phosphatase (hereinafter, sometimes referred to as ALP) in body fluids is made in the diagnoses of bone diseases such as osteoma and hepatopaphy such as obstructive jaundice.

A method for measuring alkaline phosphatase activity was reported by H. D. Kay in J. Biol. Chem. 89 235 (1930). Since then, various methods have been proposed. Among them, a method reported by E. J. King in Biochem, J. 33 1185 (1939) has given a remarkable effect of simplifying the measurement, in which aryl phosphates such as self-developable p-nitrophenyl phosphate are used as substrates.

The above measuring methods have been improved by research workers. It has been found that the optimum pH of color developing reaction is about 10, that there is a preferred type of alcohol to be allowed to coexist, and that an inorganic salt, particularly magnesium ion is preferably used as activator. The improved method is established as IFCC method [Clin. Chimica Acta (1983) 339F–367F] wherein disodium p-nitrophenyl phosphate is used as substrate.

However, the aforementioned method has disadvantages in that a solution of disodium p-nitrophenyl phosphate must be prepared at the time of measurement and is unstable and that the preservable period of the solution at 20° to 26° C. is only 8 hours at most. Further, disodium p-nitrophenyl phosphate is unstable even at a freezing temperature as reported by Amador E., et al. [J. Amer. Med., Ass. 184 953 (1963)]. Therefore, it is necessary to assay the purity of reagent just before the measurement and the reagent must be carefully preserved during the time from its preparation to the measurement.

The aforementioned problem of instability associated with p-nitrophenyl phosphate has been greatly improved by the use of organic amine salts of p-nitrophenyl phosphate disclosed in Japanese Patent Publication No. 45(1970)34872. Further, amine salts of thimolphthalein monophosphate, which have absorption spectrum in the wavelength region longer than that of p-nitrophenyl phosphate, have been synthesized by John M. Elickson et al. (Clinical Chemistry Vol. 19, No. 6, 1973, p-664). Preservability of the substrates per se has been greatly improved by these studies, and it has become possible to easily incorporate the substrate into a kit for ALP measurement.

An analytical method which can been rapidly carried out with a simple operation, has been highly desired by medical persons using results of clinical tests. For this purpose, dry analytical methods have been used in recent years, and particularly there have been developed and improved ALP measuring methods using an integral multilayer analytical element which is easy to handle.

As a typical example of the element, there is known an integral multilayer analytical element wherein a water-absorbing reagent layer containing a color reaction reagent and a hydrophilic polymer binder is provided on a transparent support and a porous spreading layer as the uppermost layer is provided on said reagent layer, proposed by B. Walter [Analytical Chemistry (1983) 55 493A]. Further, a number of elements are known.

In performing the analysis of ALP by dry analytical methods, however, the substrates such as p-nitrophenyl phosphate in the aforementioned wet analytical methods are not considered to be fully satisfactory with respect to an improvement in preservability. Accordingly, it is highly demanded to develop an integral multilayer analytical element for the measurement of alkaline phosphatase activity, in which the preservability of the substrate is satisfactorily improved.

SUMMARY OF THE INVENTION

The present inventors have made studied on conventional dry measuring methods and instruments (integral multilayer analytical elements) for alkaline phosphatase activity, and found that when a substance functioning as a basic buffer agent or a phosphoric acid acceptor is in contact with a substrate such as an amine salt of an aryl phosphate during the course of the preparation of the analytical element or the preservation thereof, there occurs great lowering of the preservability of the substrate, even if the substrate such as amine salt of the aryl phosphate is stabilized in the crystal form.

Since self-developable substrates for alkaline phosphatase are generally in the form of substituted phosphates which are electron-attractive, and the esters are liable to undergo non-enzymatic hydrolysis. Therefore, when the buffer agent buffering to a pH of about 10 to 11 which is the optimum pH for alkaline phosphatase, or the phosphoric acid acceptor containing an atom (oxygen atom of alcoholic hydroxyl group or nitrogen atom of amino group) nucleophilically attacking the phosphorus atom of phosphoric acid group is brought in contact with the substrate, the non-enzymatic hydrolysis of the substrate is accelerated.

It is an object of the present invention to provide an integral multilayer analytical element for use in the measurement of alkaline phosphatase activity, which is made free from the problems associated with dry analytical methods using conventional integral multilayer analytical elements.

It is another object of the invention to provide an integral multilayer analytical element which is easy to handle, can be rapidly operated and can be easily used for the measurement of alkaline phosphatase activity in liquid samples by unskilled persons in clinical tests.

The present invention provides an integral multilayer analytical element for use in the measurement of alkaline phosphatase activity, which comprises a porous spreading layer containing a self-developing substrate which produces a colored product in response to contact with alkaline phosphatase, a buffer layer containing a diffusion-resistant base and a support, which are preferably laminated in this order.

In the present invention, the integral multilayer analytical element for use in the measurement of alkaline phosphatase activity has such a structure that the porous spreading layer (hereinafter referred to as spreading layer) contains a self-developable substrate and the buffer layer contains a diffusion-resistant base. Said diffusion-resistant base functions as a phosphoric acid acceptor or a buffer agent. Therefore, the analytical element of the invention is almost free from the phenomenon that the substance functioning as the phosphoric acid acceptor or the buffer agent diffuses into the spreading layer and is brought into contact with the substrate during the course of the preparation of the element or the preservation thereof after the preparation.

Thus in the analytical element of the present invention, the substrate hardly undergoes non-enzymatic hydrolysis. As a result, the preservability of the substrate is greatly improved, the analytical element can be easily prepared and stability greatly increases.

Further, the analytical element of the invention has an advantage in that the measurement of ALP activity can be made with high accuracy immediately after its preparation as compared with conventional elements.

DETAILED DESCRIPTION OF THE INVENTION

A light-transmissive, water-impermeable sheet is preferred as a material constituting the support of the integral multilayer analytical element for use in the measurement of ALP activity in the present invention. Examples of such water-impermeable, light-transmissive supports include transparent support in the form of a film or sheet made of a polymer such as polyethylene terephthalate, polycarbonate of bisphenol A, polystyrene and cellulose esters (e.g., cellulose diacetate, cellulose triacetate, cellulose acetate propionate etc.). The thickness of the support generally ranges from approx. 50 μm to approx. 1 mm, preferably from approx. 80 μm to approx. 300 μm.

There may be provided an undercoating layer on the support to enhance the adhesion between the support and the buffer layer or optionally added other intervening layer (e.g., absorbent layer). Instead of the undercoating layer, the surface of the support may be activated by physical or chemical processing to enhance the adhesion.

There is provided the buffer layer on the support (optionally, intervened by other layers such as undercoating layer). The buffer layer of the analytical element for the measurement of ALP activity in the present invention is preferably a layer comprising a hydrophilic binder, that is, a layer containing a hydrophilic polymer as a layer-forming component which absorbs water to swell.

The hydrophilic polymer preferably shows swelling ratio ranging from approx. 150 % to approx. 2,000 %, more preferably from approx. 250 % to approx. 1,500 % at 30° C. Examples of the hydrophilic polymer satisfying the above-described conditions include gelatin (e.g., acidprocessed gelatin, deionized gelatin etc.), gelatin derivatives (e.g., phthalated gelatin, hydroxyacrylate grafted gelatin etc.), agarose, pullulan, pullulan derivatives, dextran, polyacrylamide, polyvinyl alcohol, and polyvinyl pyrrolidone.

The thickness of the buffer layer preferably ranges from approx. 1 μm to approx. 100 μm, more preferably from approx. 3 μm to approx. 30 μm. The buffer layer preferably is transparent.

In the present invention, the analytical element for the measurement of ALP activity is characterized in that the buffer layer contains a diffusion-resistant base, which functions as phosphoric acid acceptor or buffer agent.

Examples of such diffusion-resistant bases include basic polymers such as high-molecular weight compounds containing amino group. As the amino group, there may be mentioned primary, secondary or tertiary amino group.

When the buffer layer is formed using a basic polymer and a low-melting and water-soluble binder such as gelatin, it is necessary to form the buffer layer as a hardened film so as to bring it into a thermally stable state at the time of the measurement of the activity. In this case, a tertiary amino group is preferred as said amino group, because the primary and secondary amino groups are liable to interfere with the film-hardening reaction. For this reason, basic polymers containing a repeating unit having a tertiary amine structure are preferred as the basic polymer. Examples of such repeating units having a tertiary amine structure include those of the formula (I).

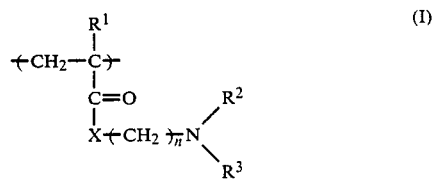

In the above formula (I), $R^1$ is hydrogen or methyl group; $R^2$ and $R^3$ are the same or different, and each represents alkyl or hydroxyalkyl group having 1 to 4 carbon atoms, or $R^2$ and $R^3$ together with the nitrogen atom to which they are attached form a nitrogen-containing sixmembered saturated heterocyclic ring; X is oxygen or —NH—; and n is 0, 1, 2, 3 or 4.

In the above formula (I), it is preferred that $R^1$ is hydrogen, n is 0, 1, 2 or 3, and $R^2$ and $R^3$ are independently methyl or ethyl or —$NR^2R^3$ forms piperidino ring. When the basic polymer contains a repeating unit of the formula (I), it is preferred that the polymer contains at least 30 mol.% of said repeating unit.

Examples of compounds, from which the repeating unit of the formula (1) may be derived, include:

acrylate monomers (in the formula (I), $R^1$ is hydrogen and X is oxygen), such as (dimethylamino)methyl acrylate, (dimethylamino)ethyl acrylate, (dimethylamino)ethyl acrylate, (dimethylamino)ethyl acrylate, (dimethylamino)propyl acrylate, morpholinoethyl acrylate, piperidinopropyl acrylate and [bis(β-hydroxyethyl)]aminopropyl acrylate;

methacrylate monomers (in the formula (I), $R^1$ is methyl and X is oxygen), such as (dimethylamino)methyl methacrylate, (diethylamino)ethyl methacrylate, (dimethylamino)ethyl methacrylate, (dimethylamino)propyl methacrylate, piperidiniopropyl methacrylate;

acrylamide monomers (in the formula (I), $R^1$ is hydrogen and X is NH), such as N-[(dimethylamino)propyl]acrylamide and N-[dipropylamino)ethyl]acrylamide; and methacrylamide monomers (in the formula (I), $R^1$ is methyl and X is —NH—) such as N-[(dimethylamino)propyl]methacrylamide.

Examples of other repeating units having a tertiary amine structure include those of the following formulas (II) and (III)

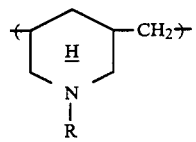

(II)

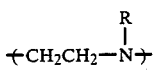

(III)

In the above formulas (II) and (III), R is an alkyl group having 1 to 4 carbon atoms.

Examples of other tertiary amines which can be used in the repeating unit include vinylpyridines such as 2-vinylpyridine and 4-vinylpyridine; and vinylimidazole derivatives such as 1-vinyl-3-alkyl-2,3-dihydroimidazole (e.g. 1-vinyl-3-alkyl-2,3-dihydroimidazole), 1-vinyl-3-aralkyl-2,3-dihydroimidazole (e.g. 1-vinyl-3-benzyl-2,3-dihydroimidazole), 2-vinyl-1-aralkylimidazole (e.g. 2-vinyl-1-methyl-imidazole and 2-vinyl-1-ethylimidazole) and 2-vinyl-1-aralkylimidazole (e.g. 2-vinyl-1-benzylimidazole)

The basic polymer containing a repeating unit having a tertiary amine structure represented by any of the above-described formulas may be a homopolymer or a copolymer. The copolymer may be composed only of repeating units represented by the above-described formulas, or a copolymer with other monomer. When a copolymer with other monomer is used, it is preferred to contain at least 30 mol% of one or more repeating units of the above formulas. Examples of other monomers include acrylamide N-substituted acrylamide, methacrylamide, N-substituted methacrylamide, ester of acrylic acid, ester of methacrylic acid, styrene, styrene derivatives, divinyl benzene and N-vinyl-pyrrolidone.

The molecular weight of the basic polymer varies depending on the type of the polymer and is chosen by taking it into consideration that when the molecular weight is too low, there is a fear of the polymer being diffused in the spreading layer, while it is too high, the compatibility of the polymer with hydrophilic colloid in the coating solution of the buffer layer becomes poor. Generally, the basic polymer is employed in such molecular weight that the solution of the polymer in 1 % aqueous sodium chloride solution has an intrinsic viscosity of 0.1 to 5.0, preferably 0.3 to 2.5 at 30° C.

The basic polymer may be used with a hydrophobic polymer in the form of an aqueous latex, or in the form of an aqueous latex or fine particles utilizing crosslinking monomer.

Further, the diffusion-resistant base may be in the form of hydrophobic latex or fine particles (e.g. various metal oxides or crystalline cellulose) having the aforementioned basic polymer, a low-molecular base or an alkaline metal salt which is absorbed on the surface.

The amount of the diffusion-resistant base to be incorporated into the buffer layer is determined by taking it into consideration that when the amount is too small, a satisfactory effect can not be obtained, while when the amount is too large, the compatibility of the basic polymer with a hydrophilic polymer in a coating solution forming the buffer layer becomes poor. Generally, the base is employed in an amount of 5 to 80 %, preferably 10 to 60 % based on the amount (on a dry weight basis) of the buffer layer.

The phosphoric acid acceptor used in the invention means to include compounds having a function capable of chemically (e.g., a neutralization reaction between acid and base) trapping phosphoric acid produced from a substrate by the action of alkaline phosphatase. Conventional phosphoric acid acceptors are compounds containing a functional group (e.g., hydroxyl group) which is caused to react with phosphoric acid produced from a substrate by the action of alkaline phosphatase before a reaction of said phosphoric acid with water (hydrolysis) takes place. On the other hand, when the diffusion-resistant base of the present invention functions as the phosphoric acid acceptor, it has effects of trapping the produced phosphoric acid so as to control an increase in the concentration of phosphoric acid in the analytical element and to obstruct a product inhibition of phosphoric acid which is a reaction product. Using a diffusion-resistant base capable of functioning as phosphoric acid acceptor, the desired reaction is promoted, the enzyme activity of an analyte increases and as a result, detection accuracy is improved.

Even when the diffusion-resistant base is used for the purpose of making it function as phosphoric acid acceptor, it is possible to allow it to function as a buffer agent capable of giving the optimum pH for the desired enzyme reaction. Accordingly, a buffer layer can be formed without adding separately a buffer agent, if desired.

Alternatively, said diffusion-resistant base may be incorporated in the buffer layer for the purpose of allowing it to function principally as buffer agent.

It is preferred to incorporate additionally at least one compound functioning as a buffer agent in the buffer layer, when the diffusion-resistant base does not function satisfactorily as buffer agent, though it functions as a phosphoric acid acceptor.

Other compounds capable of functioning as the buffer agent may be incorporated in the buffer layer. Such compound is chosen from among buffer agents which buffer to pH of about 10 to 11 (which is the optimum pH for alkaline phosphatase as analyte) and does not have an adverse effect, for example, does not inhibit reaction.

Examples of such buffer agents include known agents such as carbonate, borates, phosphates and Good's buffer agent. These buffer agents can be chosen by referring to literatures such as "Fundamental Experimental Method of Protein and Enzyme" by Takeichi Horio et al. (Nankodo, 1981) written in the Japanese language.

A hardening layer may be provided on upper side or lower side of the buffer layer to harden it. Examples of hydrophilic polymer binders which are used to form the hardening layer includes hydrophilic polymers used in the production of the buffer layer.

In the case that the water-soluble binder constituting the buffer layer is a low-melting substance such as gelatin, the buffer layer can be easily prepared by the conventional photographic film-manufacturing technique. However, such buffer layer causes dissolution or fluidization during the course of activity measurement and the measured values vary. This problem can be solved using a hardening agent (crosslinking agent) such as vinyl sulfone or an aldehyde which is known with respect to the photographic film-manufacturing technique. However, in the case that the hardening agent is directly added to a coating solution of the buffer layer buffering to a pH of 10 to 11, a crosslinking (hardening) reaction rapidly proceeds at such a high pH so that it is difficult to stably conduct coating. Therefore, it is preferred that the hardening film layer containing said hardening agent adjoins the buffer layer. When the hardening layer at the stage of coating exists at a position which allows said layer to be physically connected to the buffer layer, there are no limitations with respect to other intervening functional layer and its position whether it is provided on the upper or lower sides of the buffer layer. When the water-soluble binder is a high-melting substance such as agarose, the hardening layer may not be necessary.

There may be provided a light-blocking layer on the buffer layer or the hardening layer. The light-blocking layer is a water-permeable layer in which light-blocking (or light-reflecting) fine particles are dispersed in an small amount of a film-forming hydrophilic polymer binder. The light-blocking layer may function as lightreflecting layer or background layer as well as blocker to the color of an aqueous liquid spotted on the spreading layer, such as the red of hemoglobin in a whole blood sample, when a detectable change (a color change or a color development etc.) in the buffer layer is measured from the side of the transparent support in reflection photometry.

Examples of light-blocking and light-reflecting particle include titanium dioxide fine particles (rutiletype, anatase-type or brookite-type; means size ranging from approx. 0.1 $\mu$ to approx. 1.2 $\mu$), barium sulfate fine particles, aluminum fine particles and fine flakes thereof. Examples of light-blocking particle include carbon black, gas black and carbon microbeads. Most preferred are titanium dioxide fine particles and barium sulfate fine particles.

Examples of the film-forming hydrophilic polymer binder include a weakly hydrophilic polymer such as regenerated cellulose and cellulose acetate as well as the hydrophilic polymer employable in the buffer layer. Most preferred are gelatin, gelatin derivatives and polyacrylamide. Gelatin and gelatin derivatives may be used as a mixture with a known hardening agent (cross-linking agent).

The light-blocking layer can be provided in such a manner than an aqueous dispersion containing the light-blocking particle and the hydrophilic polymer is coated on the buffer layer and then dried by any of the conventional methods. Instead of the light-blocking layer, the light-blocking particles may be incorporated into the spreading layer.

There may be provided an adhesive layer on the buffer layer or optionally added other layer (e.g., light-blocking layer) to enhance the adhesion of the spreading layer.

The adhesive layer is preferably constituted by a hydrophilic polymer which can bond the spreading layer to other layer to make all of the layers integrated while the polymer is wet or swelled with water. Examples of the hydrophilic polymers include the polymers employable in the buffer layer. Most preferred are gelatin, gelatin derivatives and polyacrylamide. The dry thickness of the adhesive layer generally ranges from approx. 0.5 $\mu$ to approx. 20 $\mu$, preferably from approx. 1 $\mu$ to approx. 10 $\mu$.

The adhesive layer may be provided on other layers as well as on the buffer layer. The adhesive layer can be prepared in such a manner that a solution of a hydrophilic polymer and optionally added other agent such as a surfactant is coated on the reaction layer or other layer.

A porous spreading layer of woven fabric or knitted fabric is provided on the layer. The spreading layer preferably has a metering effect (i.e., metering the spotted liquid sample). The term "spreading layer capable of metering a liquid sample" herein used refers to a layer having a function capable of spreading an applied liquid in such a manner that the spread area of the liquid is approximately in proportion to the amount of the liquid when the liquid is applied thereon and further having a function capable of supplying the liquid to the buffer layer. Preferably, the porous spreading layer of the invention should be one having voids capable of expanding and allowing alkaline phosphatase as an analyte to be passed therethrough.

Examples of materials constituting the matrix of the porous spreading layer of the integral multilayer analytical element for use in the measurement of ALP activity include filter paper, nonwoven fabric, woven fabric, knitted fabric, glass fiber, membrane filter and threedimensional lattice structure composed of the microbead of a polymer.

The matrix of the spreading layer is chosen from the above-described materials according to the analytical conditions. When the sample containing insoluble materials which are inhibitors to the analysis (e.g., whole blood containing blood cell) is applied, the woven fabric and the knitted fabric which have a function to eliminate such inhibitors are most advantageous.

Examples of the woven fabrics (woven cloth) which can be used for the porous reagent layer include those disclosed in Japanese Patent Provisional Publication No. 55(1980)-164356 and No. 57(1982)-66359. Among the woven fabrics, plain weave fabrics made of warp and weft are preferred. Among plain woven fabrics, thin cloth, muslin, broadcloth and poplin are preferred.

Examples of yarns for woven cloth include those composed of the same materials as those constituting knitted cloths as described in more detail hereinafter. Any of filament yarn and spun yarn (twist yarn) can be used, and the spun yarn is preferred. The yarn diameter of the woven fabric is generally in the range of about 20S to about 150S, preferably about 40S to about 120S in terms of cotton spinning yarn count or in the range of about 35 to about 300D, preferably about 45 to about 130D in terms of silk thread denier. The thickness of the woven fabric is generally in the range of about 100 to about 500 $\mu$, preferably about 120 to 350 $\mu$. The voids of the woven fabric are generally in the range of about 40 to about 90%, preferably about 50 to about 85%.

Examples of the knitted fabrics which can be used for the porous reagent layer include many kinds of knitted fabrics, among which warp knitted fabric and weft knitted fabric are preferred. Examples of the warp knitted fabrics include single atlas knitted cloth, tricot knitted cloth, double tricot knitted cloth, milanese knitted cloth and rashar knitted cloth. Examples of the weft knitted fabrics include plain weave knitted cloth, pearl knitted cloth, rib stitch cloth, and double face knitted cloth. Examples of the yarns for knitted fabrics include yarns of natural fibers such as cotton, silk and wool; yarns composed of fine fibers or single fibers of regenerated cellulose (e.g. viscose rayon and cupra), semi-synthetic organic polymer (e.g., cellulose diacetic and cellulose triacetate), synthetic organic polymer (e.g., polyamide such as nylon, acetalated polyvinyl alcohol such as vinylon, polyacrylonitrile, polyethylene terephthalate, polyethylene, polypropylene and polyurethane), and yarns composed of fiber blends of a natural fiber and a regenerated cellulose or a semi-synthetic or synthetic organic polymer fiber. Any of filament yarn and spun yarn can be used, and spun yarn is preferred. The diameter of the yarn for knitted fabric is generally in the range of from about 40 to 150S, preferably about 60 to about 120S in terms of cotton spinning yarn count, or in the range of about 35 to about 130D, preferably about 45 to about 90D in terms of silk thread denier. The number of knitting gauge of the knitted fabric is generally in the range of about 20 to about 50. The thickness of the knitted fabric is generally in the range of about 100 to about 600 $\mu$, preferably about 150 to about 40 $\mu$. The voids of the knitted fabric are generally in the range of about 40 to about 90%, preferably about 50 to about 85%. The yarn knitted fabric, tricot knitted cloth, rashar knitted cloth, milanese knitted cloth and double tricot knitted cloth are preferred, because shrinkage in the wale's direction is small, the operation in the lamination stage of knitted goods is easy and the stitches are not easily loosened during cutting.

Woven fabric or knitted fabric is preferably a fabric from which fat is substantially removed when the yarn or the fabric is prepared. The fabrics are more preferably processed to be hydrophilic to enhance the adhesion to an underlying layer. Examples of such process to make the fabric hydrophilic include physical activating process (preferably glow discharge process or corona discharge process) disclosed in Japanese Patent Provisional Publication No. 57(1982)-66359 and hydrophilic polymer permeating process disclosed in Japanese Patent Provisional Publication Nos. 55(1980)-164356 and 57(1982)-66359.

The spreading layer formed of woven fabric or knitted fabric can be laminated on the buffer layer or the adhesive layer according to the process disclosed in Japanese Patent Provisional Publications No. 55(1980)-164356 and No. 57(1982)-66359. The process is that woven fabric or knitted fabric is laminated under the substantially uniform light pressure on the wet or swelling buffer layer or adhesive layer which has been still wet condition after coating or has been supplied with water (or water containing small amount of detergent) after drying.

When the buffer layer or the adhesive layer is made of gelatin or gelatin derivatives, the spreading layer made of woven fabric or knitted fabric is preferably laminated on the wet or swelling gelatin (or its derivatives) of reaction layer or adhesive layer which has been still wet condition after coating.

In the analytical element of the present invention a self-developable substrate is incorporated into the spreading layer. The term "self-developable substrate" used herein means a substance which undergoes hydrolysis as a substrate for alkaline phosphatase to develop a detectable color or to produce a color change. As the self-developable substrate, the amine salts of aryl phosphates are preferred from the viewpoint of preservability. Among them, there are particularly preferred the mono- or diamine salts of monoaryl phosphate which exhibit absorption spectrums in the visible ray region of 40 nm or above by hydrolysis reaction of alkaline phosphatase.

Examples of aryl phosphates which can form said self-developable aryl phosphate amine salts include -nitrophenyl phosphate, phenolphthalein monophosphate, thymolphthalein monophosphate and o-methylfluorescein phosphate described in the literature by Bower G. N. [Clin. Chem. Vol. 14, No. 7, 608–610 (1967)] and arylazo-substituted aryl phosphates disclosed in Japanese Patent Provisional Publication No. 57(1982)-159499.

Examples of the self-developable aryl phosphate amine salts include bis(2-amino-2-methyl-1,3-propandiol) salt of p-nitrophenyl phosphate, bis(cyclohexylamine) salt of p-nitrophenyl phosphate, bis(2-amino-2-ethyl-1,3-propanediol) salt of p-nitrophenyl phosphate, bis(dicyclohexylamine) salt of p-nitrophenyl phosphate, ditris salt (the term "tris" means tris(hydroxymethyl)aminomethane) or p-nitrophenyl phosphate, bis(2-amino-2-ethyl-1,3-propanediol) salt of 4-nitronaphthyl phosphate, bis(cyclohexylamine) salt of thymolphthalein monophosphate, bis(2-ethylaminoethanol) salt of 4-phenylazonaphthyl phosphate, bis(N-methyl-glucamine) salt of phenolphthalein monophosphate, bis(2-amino-2-ethylpropanol) salt of 4-nitrophenyl monophosphate, bis(2-ethylethanol) salt of 4-nitrophenyl monophosphate and bis(2-(isopropylamino)ethanol) salt of 4-nitrophenyl monophosphate.

It is desired that the self-developable substrate is incorporated in the spreading layer in such a manner that the substrate is not brought into contact with the buffer agent of the buffer layer. For instance, said substrate, optionally together with a surfactant and a high-molecular compound is dissolved in an organic solvent or a mixture of an organic solvent and water to obtain a coating solution. The coating solution is then coated on the spreading layer of a laminate obtained by laminating the buffer layer and then the spreading layer onto a support. Alternatively, the spreading layer is impregnated with said coating solution.

Examples of the organic solvents include watersoluble polar solvents such as ethanol, methanol, propanol, acetone and acetonitrile; and hydrophobic solvents such as toluene and ethyl acetate.

When the spreading layer is composed of a material to be laminated such as woven fabric, nonwoven fabric, knitted fabric, filter paper or glass fiber, it may be previously impreganated with the substrate, dried and then laminated. When the spreading layer is formed by coating, for instance, the spreading layer is composed of a brush polymer layer or a three-dimensional lattice particle structure composed of microbeads, a mixture consisting of the coating solutions of the substrate and the spreading layer may be applied. In addition to said substrate, light-blocking particles or reagents such as surfactant may be incorporated into the spreading layer. These reagents may be mixed with the coating solution of the substrate and then applied to the spreading layer. Alternatively, said reagents may be separately applied.

The integral multilayer analytical element of the present invention comprises a support, a buffer layer and a spreading layer in the form of a laminate, and it is preferred that these layers are laminated in the abovedescribed order. If desired, the analytical element of the present invention may contain other functional layers.

The following examples and comparison example are provided to illustrate the present invention without limiting it thereto.

EXAMPLE 1

A surface of a transparent polyethylene terephthalate support of 180 $\mu$ thick was treated to make it hydrophilic. The treated surface was then coated with a coating solution having the following composition and dried to form a buffer layer having a dry film thickness of 15 μ.

| Coating Solution for the Formation of the Buffer Layer | |
|---|---|
| Alkali-treated deionized gelatin | 24 g. |
| Water | 240 g. |
| Nonylphenoxy polyglycidol | 1.6 g. |
| Poly(N—[(dimethylamino)propyl]acrylamide) (18% aqueous solution) (average molecular weight: about 100,000) | 30 g. |
| N—(2-hydroxyethyl)ethylenediamine-N,N',N'—triacetic acid | 2 m mol. |
| $Zn(CH_3COO)_2 \cdot 2H_2O$ | 1 m mol. |
| $MgSO_4 \cdot 7H_2O$ | 2 m mol. |

The pH of the above solution was adjusted to 11.0 by adding 5N aqueous solution of NaOH.

The surface of the buffer layer was coated with the following coating solution in such an amount as to give a layer having a dry film thickness of 3.6 μ. The coated surface was dried to form a hardening layer.

| Coating Solution for the Formation of the Hardening Layer | |
|---|---|
| Gelatin | 12 g. |
| Water | 268 g. |
| Nonylphenoxy polyglycidol | 1.3 g. |
| 1,2-Bis(vinylsulfonylacetamide)ethane | 0.72 g. |
| Water/acetone (mixing ratio = 1:1) | 18 g. |

The surface of the hardening layer was coated with the following coating solution in such an amount as to give a layer having a dry film thickness of 3 μ, thus forming an adhesive layer.

| Coating Solution for the Formation of the Adhesive Layer | |
|---|---|
| Gelatin | 12 g. |
| Water | 286.7 g. |
| Nonylphenoxy polyglycidol | 1.3 g. |

The surface of said adhesive layer was coated with an aqueous solution of 0.4 % nonylphenoxy polyglycidol. A tricot knitted fabric composed of polyethylene terephthalate spun yarn (36 gauge, 50D) was laminated onto the coated surface under pressure to form a spreading layer.

The surface of the spreading layer was coated with a coating solution having the following composition in an amount of 120 ml/m² and dried.

| Coating Solution Containing Self-Developable Substrate | |
|---|---|
| Bis(tris)salt of p-nitrophenyl phosphate | 50 m mol. |
| Polyvinyl pyrrolidone (average molecular weight: 100,000) | 6 g. |
| Ethanol | 22 g. |
| Acetone | 22 g. |

In this way, an integral multilayer analytical element for use in the measurement of ALP activity according to the present invention, was prepared.

The analytical element was cut into 15 mm square tips and enclosed in a plastic mount (disclosed in Japanese patent Provisional Publication No 57(1982)-63452) to prepare a slide for the analysis of ALP.

10 μl of each of human serums containing ALP at a concentration (value assayed at 37° C.) of 100, 207, 368, 614, 922 and 1182 IU/l, which was measured according to IFCC method as standard analytical method for the measurement of ALP activity, was spotted on the spreading layer of the analytical element in the amount. Each analytical element was then allowed to stand on a constant temperature hot plate (37°C) under such conditions that moisture deposition was satisfactorily controlled. The optical reflection density of each element was measured with a light having central wavelength of 410 nm in two minutes and five minutes. The measurement results are shown in Table 1.

TABLE 1

| ALP activity (IU/l) | ΔOD (5 min.–2 min.) |
|---|---|
| 110 | 0.028 |
| 207 | 0.050 |
| 368 | 0.086 |
| 614 | 0.140 |
| 922 | 0.188 |
| 1182 | 0.223 |

It is evident from the above results that there is positive correlation between the increase of optical density and ALP activity. Thus, it has been found that the analytical element of the present invention is effective in the measurement of ALP activity.

The serums of inpatients were used as specimens, and multi-specimen test was made by using the analytical element of the present invention. The correlation of the analytical results with those obtained by using RA 1000 manufactured by Technicon Corp. (AMP buffer, p-nitrophenyl phosphate), was examined.

The results of the measurement are as follows:

| | |
|---|---|
| y = 1.267x + 92.0 | formula of straight regression |
| r = 0.991 | coefficient of correlation |
| Syx = 15.1 | standard deviation of sample from regression |
| n = 99 | the number of specimens (the number of samples) | wherein x is the measured value obtained using the analytical element of Example 1.

It is apparent from the above results that the analytical element of the invention is well-correlated to the standard method of measurement.

EXAMPLE 2

The procedure of Example 1 was repeated except that 18 % aqueous solution of poly(N-[(dimethylamino)propyl]acrylamide) in the coating solution for the formation of the buffer layer was used in an amount of 90 g. in place of 30 g. to prepare an analytical element according to the present invention. The analytical performance was evaluated.

It had been found that the slide of this Example was also effective as the analytical element for the measurement of ALP activity. The optical reflection density of the element was measured in a similar manner to that of Example 1. The results are shown in Table 2.

TABLE 2

| 20 Slide | ΔOD (5 min.–2 min.)/U |
|---|---|
| Example 1 | $1.89 \times 10^{-4}$ |
| Example 2 | $2.04 \times 10^{-4}$ |

It is apparent from Table 2 that sensitivity becomes higher with increase in the amount of poly(N,N-dimethylaminopropylacrylamide), when there is made a comparison between Example 1s and 2 in the increase in OD per unit (i.e., ΔOD (5 min.–2 min.)/U).

EXAMPLE 3

The procedure of Example 1 was repeated except that 30 mM of 2-amino-2-methyl-1,3-propanediol was added to the composition of the coating solution for the formation of the buffer layer to prepare an analytical element according to the invention. The analytical performance thereof was evaluated.

It has been found that the slide of this Example is also effective as the analytical element for the measurement of ALP activity. An increase in OD per unit was determined in the same manner as in Example 2. The results are shown in Table 3.

TABLE 3

| Slide | ΔOD (5 min.–2 min.)/U |
|---|---|
| Example 1 | $1.89 \times 10^{-4}$ |
| Example 3 | $2.40 \times 10^{-4}$ |

It is apparent from Table 3 that there is increase in sensitivity by the addition of 2-amino-2-methyl-1,3-propanediol.

COMPARISON EXAMPLE

The procedure of Example 1 was repeated except that a coating solution having the following composition to form the buffer layer was used in place of that of Example 1 to prepare an analytical element for the measurement of ALP activity.

| | |
|---|---|
| Alkali-treated deionized gelatin | 30 g. |
| Water | 240 g. |
| Nonylphenoxy polyglycidol | 1.6 g. |
| N—(2-Hydroxyethyl)ethylenediamine-N,N′, N′—triacetic acid) | 2 m mol. |
| Zn(C$_2$H$_3$OO)$_2$.2H$_2$O | 1 m mol. |
| MgSO$_4$.7H$_2$O | 2 m mol. |
| Sodium Carbonate | 3.18 g. (0.1 mol.) |

The pH of the above solution was adjusted to 11.0 by adding 5N aqueous solution of NaOH.

For the purpose of comparison, the analytical performance of the element of this Comparison example was evaluated. An increase in OD per unit was determined in the same manner as in Example 2. The results are shown in Table 4.

TABLE 4

| Slide | ΔOD (5 min.–2 min.)/U |
|---|---|
| Example 1 | $1.89 \times 10^{-4}$ |
| Comparison Example | $2.41 \times 10^{-4}$ |

Further, there was made comparison of preservability between the slide of the analytical element of the present invention and that of the Comparison Example. The results are shown in Table 5.

TABLE 5

| Slide | ΔOD (45° C., 24 hrs.-immediately after preparation) |
|---|---|
| Example 1 | 0.019 |

TABLE 5-continued

| Slide | ΔOD (45° C., 24 hrs.-immediately after preparation) |
|---|---|
| Comparision Example | 0.160 |

In Table 5, the value of ΔOD(45° C., 24 hrs. - immediately after preparation) corresponds to a value (fog optical reflection density ) = [optical reflection density obtained by preserving the analytical element at 45° C. for 24 hours and then carrying out incubation at 37° C. for 5 minutes] minus [optical reflection density obtained by carrying out at 37° C. for 5 minutes the incubation of the analytical element immediately after preparation], the liquid sample being not deposited.

As shown in Table 4, the analytical element of Comparative Example is effective in the measurement of ALP activity with respect to sensitivity. With regard to preservability, however, the element of Comparison Example is not considered that it is satisfactory as the analytical element for the measurement of ALP activity as is clear from Table 5.

EXAMPLE 4

The procedure of Example 1 was repeated except that an equal amount of poly(N-[)diethylamino)propyl]acrylamide) was used in place of poly(N-[)dimethylamino)propyl]acrylamide) in the coating solution for the formation of the buffer layer to prepare an analytical element of the present invention. The analytical performance was then evaluated.

The slide of this Example had good performance as the element for the measurement of ALP activity similar to those of Examples 1, 2 and 3.

EXAMPLE 5

The procedure of Example 1 was repeated except that an equal amount of bis(2-amino-2-ethyl-1,3-propanediol) salt of p-nitrophenyl phosphate was used in place of bis(tris) salt of p-nitrophenyl phosphate in the coating solution containing a self-developable substrate to prepare an analytical element according to the invention. The analytical performance was then evaluated.

The slide of this Example had good performance as the element for the measurement of ALP activity similar to those of Examples 1, 2, 3 and 4.

EXAMPLE 6

A rise in the optical reflection density of the analytical elements of Examples 1, 2 and 3 and Comparison Example after 24 hours (I) and 7 days (II) at 45° C. was determined to compare their preservability with one another. The results are shown in Table 6.

TABLE 6

| Slide | ΔOD (I) | ΔOD (II) |
|---|---|---|
| Example 1 | 0.019 | 0.060 |
| Example 2 | 0.015 | 0.059 |
| Example 3 | 0.083 | 0.220 |
| Comparison Example | 0.160 | 0.245 |

In Table 6, the value of ΔOD(I) corresponds to a value (fog optical reflection density ) = [optical reflection density obtained by preserving the analytical element at 45° C. for 24 hours and then carrying out incubation at 37° C. for 5 minutes] minus [optical reflection density obtained by carrying out at 37° C. for 5 minutes the incubation of the analytical element immediately after preparation], the liquid sample being not spotted. The value of ΔOD(II) corresponds to a value (fog optical reflection density)] [optical reflection density obtained by preserving the analytical element at 45° C. for 7 days and then carrying out incubation at 37° C. for 5 minutes]minus [optical reflection density obtained by carrying out at 37° C. for 5 minutes the incubation of the analytical element immediately after preparation], the liquid sample being not spotted.

It is apparent from the above results that the analytical elements of Examples 1, 2 and 3 according to the present invention have good preservability. Further, the analytical elements of Examples 4 and 5 were tested and it had been found that they had good preservability equal to that of the element of Example 1.

EXAMPLE 7

The procedure of Example 1 was repeated except that each of diffusion-resistant based given in Table 7 was used in place of poly(N-[(dimethyl-amino)propyl]acrylamide in the coating solution for the formation of the buffer layer to prepare an integral multilayer analytical element for the measurement of ALP activity according to the present invention. The analytical performance of each element was evaluated. They had good performance similar to those of Examples 1, 2, 3 and 4.

The diffusion-resistant bases (1 to 4) of Table 7 were the following polymers.
(1) Poly(dimethylamino)ethyl acrylate
(2) (Dimethylamino)propyl acrylate/acrylamide (5:2) copolymer
(3) Polypiperidinopropyl acrylate
(4) (Diethylamino)ethyl acrylate/acrylamide (1:1) copolymer

TABLE 7

| Diffusion-resistant base | Degree of polymerization | Net content in coating solution |
|---|---|---|
| 1 | 2.5 | 6 g. |
| 2 | 1.8 | 10 g. |
| 3 | 0.9 | 15 g. |
| 4 | 0.5 | 20 g. |

We claim:

1. An integral multilayer analytical element for the measurement of alkaline phosphatase activity, which comprises a porous spreading layer containing a self-developable substrate in response to contact with alkaline phosphatase, a buffer layer containing a diffusion-resistant basic polymer containing a repeating unit having a tertiary amine structure and a support in a laminated form with said buffer layer being positioned between said porous spreading layer and said support.

2. The integral multilayer analytical element as claimed in claim 1, wherein said basic polymer contains a repeating unit of the following formula (I):

$$\mathrm{+CH_2-\underset{\underset{X+CH_2\xrightarrow{}_n N\underset{R^3}{\diagdown}R^2}{\overset{|}{C=O}}}{\overset{R^1}{\underset{|}{C}}}\xrightarrow{}} \quad (I)$$

wherein $R^1$ is hydrogen or methyl group; $R^2$ and $R^3$ are the same or different, and each represents an alkyl or hydroxyalkyl group having 1 to 4 carbon atoms, or $R^2$ and $R^3$ together with the nitrogen atom to which they are attached form a six-membered saturated heterocyclic ring; X is oxygen or —NH—; and n is 0, 1, 2, 3 or 4.

3. The integral multilayer analytical element as claimed in claim 2, wherein said basic polymer contains at least 30 mol % of said repeating unit of the formula (I) wherein $R^1$ is hydrogen; $R^2$ and $R^3$ are the same or different, and each represents methyl or ethyl group, or $R^2$ and $R^3$ together with the nitrogen atom to which they are attached form a piperidino group; X is oxygen or —NH—; and n is 0, 1, 2 or 3.

4. The integral multilayer analytical element as claimed in claim 1, wherein said basic polymer has an intrinsic viscosity measured in 1% aqueous sodium chloride solution at 30° C. in the range of 0.1 to 5.0.

5. The integral multilayer analytical element as claimed in claim 1, wherein said buffer layer contains 5 to 80 % by weight of the diffusion-resistant basic polymer.

6. The integral multilayer analytical element as claimed in claim 1, wherein said self-developable substrate is an amine salt of an aryl phosphate.

7. The integral multilayer analytical element as claimed in claim 6, wherein said amine salt of the aryl phosphate contains an aryl group selected from the group consisting of nitro-substituted phenyl, phenolphthalein, thymolphthalein, arylazo-substituted aryl and fluorescein and an amine selected from the group consisting of tris(hydroxymethyl)-aminomethane, 2-amino-2-methyl-1,3-propanediol, 2-amino-2-ethyl-1,3-propanediol, bis(cyclohexyl)amine, 2-(ethylamino)ethanol, N-methylglucamine, 2-(methylamino)ethanol, 2-(dimethylamino)ethanol, 2-(isopropylamino)ethanol and 2-amino-2-methyl-1-propanol.

8. The integral multilayer analytical element as claimed in claim 1 wherein said basic polymer is one functioning as a phosphoric acid acceptor and a buffer agent.

9. The integral multilayer analytical element as claimed in claim 1 wherein said basic polymer is one functioning as a phosphoric acid acceptor and a buffer agent and said buffer layer further contains at least one buffer agent.

10. The integral multilayer analytical element as claimed in claim 1 wherein said basic polymer contains a repeating unit of the following formula (II):

$$\mathrm{+\underset{\underset{\underset{R}{|}}{N}}{\overset{H}{\diagup}\diagdown}CH_2+}$$

wherein R is an alkyl group having 1 to 4 carbon atoms.

11. The integral multilayer analytical element as claimed in claim 1 wherein said basic polymer contains a repeating unit of the following formula (III):

$$\mathrm{+CH_2CH_2-\underset{\underset{R}{|}}{N}+} \quad (III)$$

wherein R is an alkyl group having 1 to 4 carbon atoms.

12. The integral multilayer analytical element as claimed in claim 1 wherein said basic polymer contains a repeating unit derived from a tertiary amine selected from the group consisting of vinylpyridines and vinylimidazole derivatives.

* * * * *